United States Patent
O'Quinn et al.

(10) Patent No.: US 6,893,448 B2
(45) Date of Patent: May 17, 2005

(54) ENDOSCOPIC CAPSULAR SUTURE PLICATION INSTRUMENT AND METHOD

(75) Inventors: Philip S. O'Quinn, Naples, FL (US); Robert M. Weber, Chino Hills, CA (US); Reinhold Schmieding, Naples, FL (US)

(73) Assignee: Arthrex, Inc., Naples, FL (US)

( * ) Notice: Subject to any disclaimer, the term of this patent is extended or adjusted under 35 U.S.C. 154(b) by 217 days.

(21) Appl. No.: 10/277,678

(22) Filed: Oct. 23, 2002

(65) Prior Publication Data

US 2003/0078599 A1 Apr. 24, 2003

Related U.S. Application Data

(60) Provisional application No. 60/350,034, filed on Jan. 23, 2002, and provisional application No. 60/330,490, filed on Oct. 23, 2001.

(51) Int. Cl.$^7$ .............................................. A61B 17/10
(52) U.S. Cl. ....................... 606/139; 606/144; 606/148; 606/223
(58) Field of Search ................................ 606/139, 144, 606/148, 222, 223

(56) References Cited

U.S. PATENT DOCUMENTS

| | | | |
|---|---|---|---|
| 5,059,201 A | | 10/1991 | Asnis |
| 5,431,666 A | * | 7/1995 | Sauer et al. ................ 606/139 |
| 5,522,820 A | | 6/1996 | Caspari et al. |
| 5,562,686 A | * | 10/1996 | Sauer et al. ................ 606/144 |
| 5,665,096 A | * | 9/1997 | Yoon .......................... 606/139 |
| 6,533,796 B1 | * | 3/2003 | Sauer et al. ................ 606/144 |

* cited by examiner

Primary Examiner—Glenn K. Dawson
Assistant Examiner—Darwin P. Erezo
(74) Attorney, Agent, or Firm—Dickstein Shapiro Morin & Oshinsky, LLP

(57) ABSTRACT

An instrument for surgical suturing includes a shaft, and a needle disposed slidably for longitudinal travel with respect to the shaft. A prong formed on one end of the shaft projects across a longitudinal axis of the needle and has an opening formed through the prong that provides a clearance through which a tip portion of the needle passes when it is advanced. Slots formed on a surface of the prong facing the shaft releasably hold suture across the opening. The suture is held in the slots by passing the suture strands separately back around the sides of the prong, then together up through a channel formed on the prong above the slots, and securing the strands in a pinch slot formed in a handle of the instrument. Advancing the needle through the clearance allows a hook formed on the tip of the needle to capture the suture. Once withdrawn, the needle draws the suture back through tissue pierced during advancement. The suture is released from the slots and drawn back through the tissue for further knot tying and suturing to effect the tissue repairs.

11 Claims, 6 Drawing Sheets

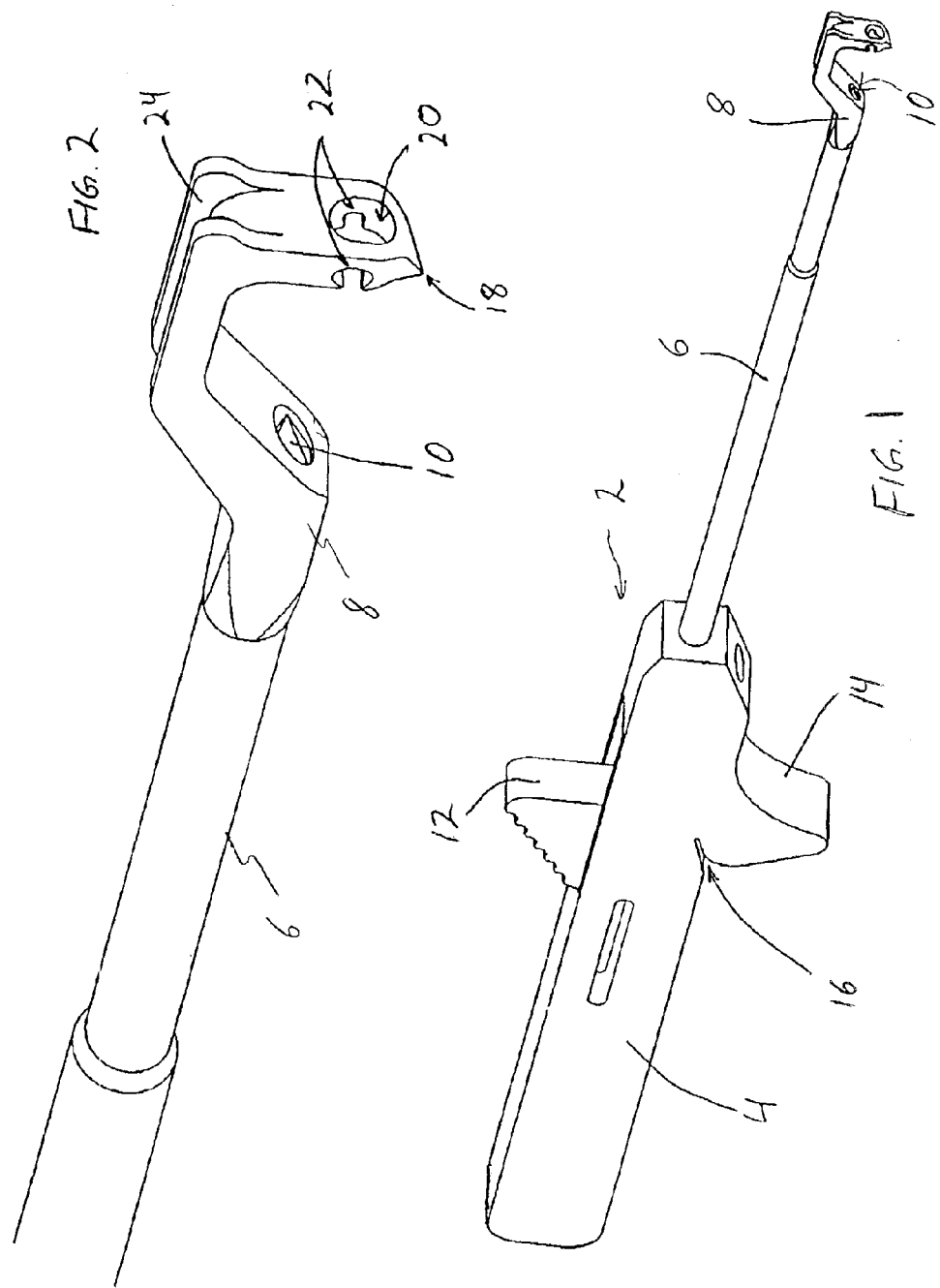

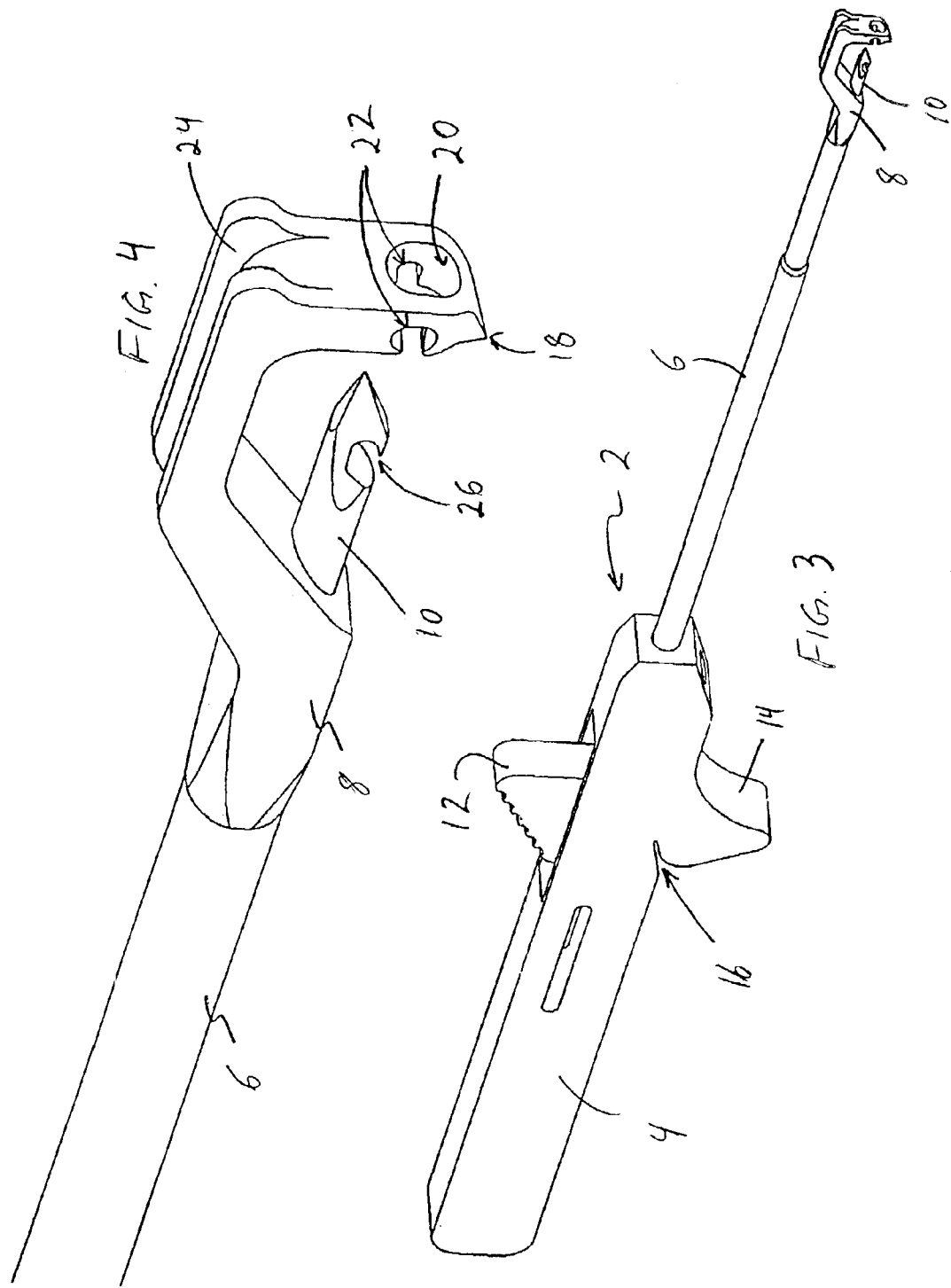

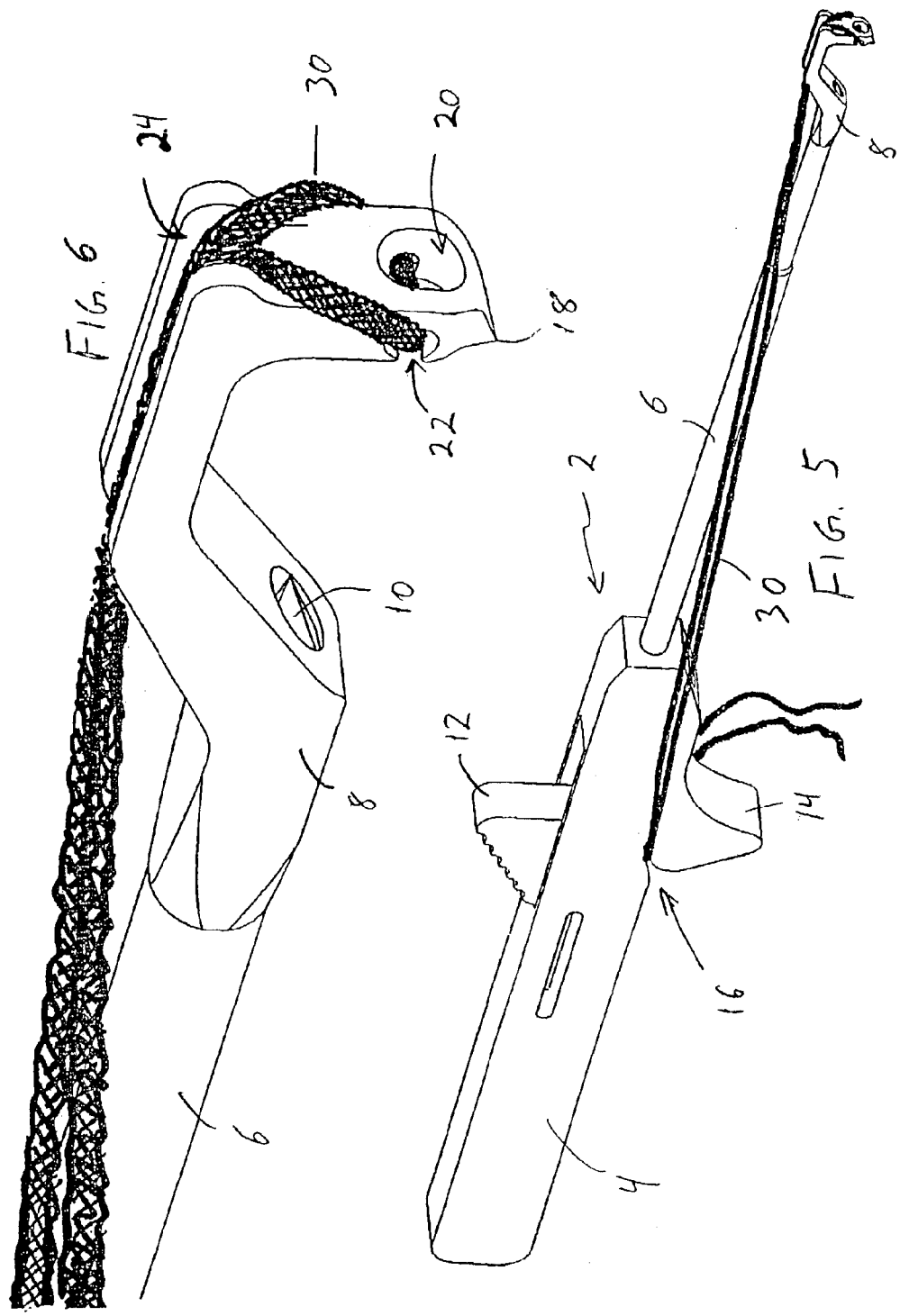

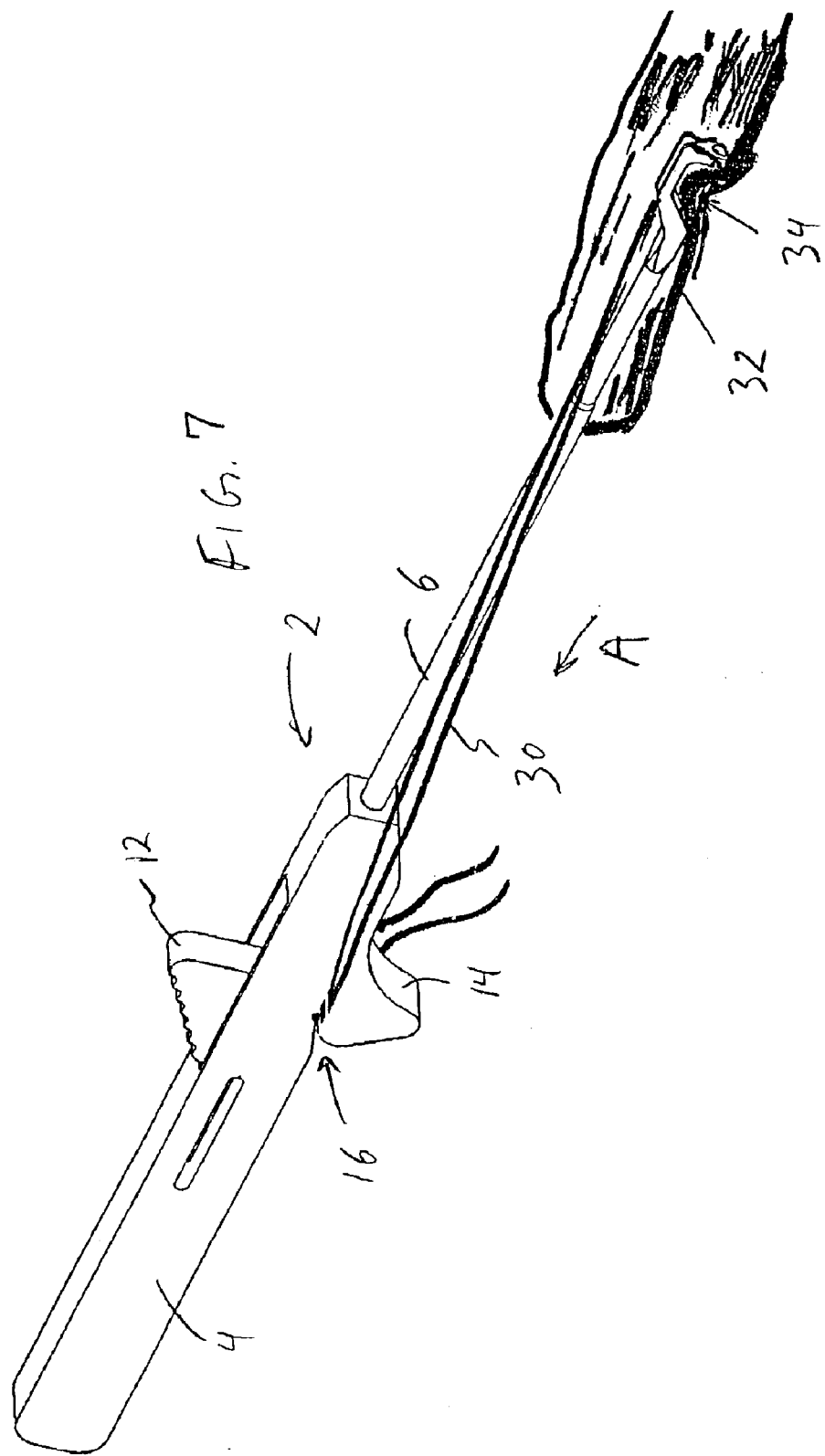

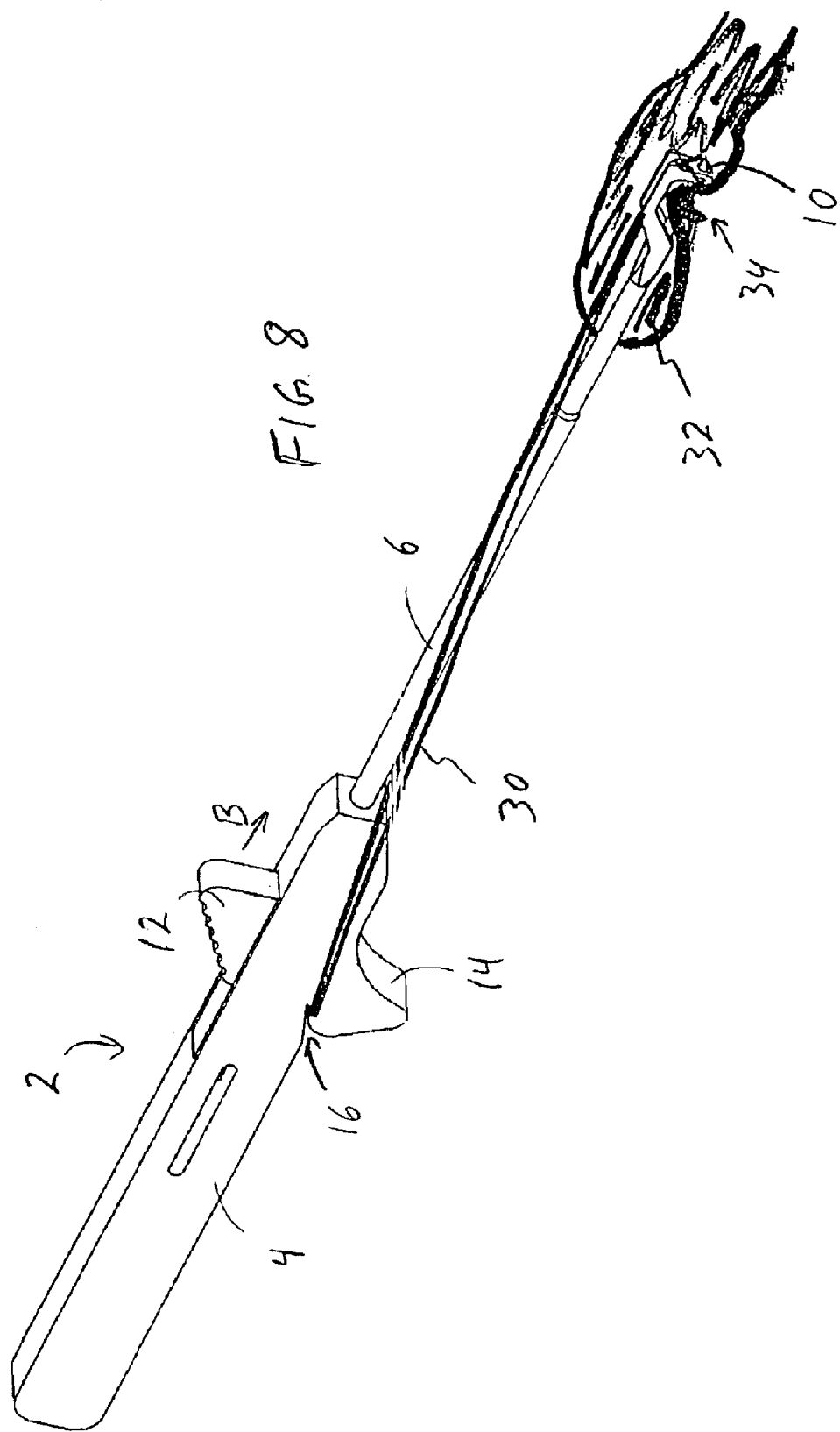

ENDOSCOPIC CAPSULAR SUTURE PLICATION INSTRUMENT AND METHOD

This application claims the benefit of U.S. Provisional Application No. 60/330,490, filed Oct. 23, 2001, and U.S. Provisional Application No. 60/350,034, filed Jan. 23, 2002.

BACKGROUND OF THE INVENTION

1. Field of the Invention

The invention relates to endoscopic suturing, and more particularly to instruments for arthroscopic repair of torn tissue, such as glenoid repair and capsular suture plication.

2. Description of the Related Art

Intracorporeal suturing, particularly suturing tissue during arthroscopic surgery, presents challenges to a surgeon who must manipulate suturing instruments in confined spaces and through a relatively small incision. One device which has been developed for facilitating suturing during arthroscopic surgery is disclosed in U.S. Pat. No. 4,890,615. This instrument has a cannulated or hollow needle secured to a jaw positioned near the end of a long tube. The jaw can be manipulated by a hand grip to press the needle through the tissue to be sutured. Suture material is then fed through the tube from a spool attached to the hand grip into the hollow needle and therefore through the tissue. Enough suture material is advanced through the needle so that when the needle is withdrawn from the tissue and the instrument is removed from the incision, a portion of the suture material remains within the tissue. The suture material is then tied in a manner well-known in the art so as to secure the suture material to the tissue.

While the suture punch of U.S. Pat. No. 4,890,615 generally is effective in suturing tissue, there are several disadvantages associated with using this instrument. For example, the instrument requires manually advancing the suture material through the needle by manipulating the spool, which is often somewhat difficult to do during surgery. In addition, the surgeon must verify that enough suture material has been advanced through the needle so that when the instrument is withdrawn from the incision, the suture material is not inadvertently pulled through the tissue. Furthermore, because the suture material must be fed up and through a hollow needle, tissue or other debris present in the surgical site may block the opening in the needle, making it difficult to pass the suture material through the needle. In addition, because rotating the spool against the braided suture material tended to cause the braided suture material to expand such that it was unable to pass through the tube, only monofilament suture material can generally be used. This is disadvantageous because braided suture material is generally stronger than monofilament suture material. Finally, this particular instrument cannot generally be used to simultaneously pass several segments of suture material through the tissue, which is required for certain types of sutures such as a mattress suture.

The Caspari suture punch, disclosed in U.S. Pat. No. 5,522,820, was developed to provide a suturing instrument for arthroscopic surgery without the above-noted disadvantages. The Caspari suture punch is a hand instrument with a pivotable jaw and a stationary jaw. The stationary jaw is provided with a needle that extends upwardly and has a hook on the proximal side. With the jaws closed, suture is threaded through an aperture in the movable jaw, such that the suture is disposed on the distal side of the needle of the lower jaw and is not engaged by the hook. The instrument is inserted through a relatively small incision in the patient with the jaws closed. With the jaws positioned adjacent the tissue to be sutured, the surgeon opens the jaws (by manipulating the finger grip of the instrument disposed outside the patient), and then closes the jaws to engage the tissue to be sutured. As this occurs, the needle penetrates the tissue to be sutured, and the suture is captured in the hook of the needle. When the movable jaw is then opened, the suture, which is captured in the hook, is drawn through the tissue. The instrument is then removed from the incision and the suture is secured around the tissue with a knot.

While the Caspari punch avoids some of the disadvantages of the prior spool-fed suture punch, it is directed to applications in which the tissue to be sutured must be grasped, and thus requires a movable jaw mechanism. It would be desirable to provide an instrument for suturing which does not require a movable jaw mechanism and is suitable for applications such as rotator cuff repair or surgical plication of a capsule, i.e., capsulorrhaphy.

SUMMARY OF THE INVENTION

The present invention provides an instruments and method for suturing tissue arthroscopically, in particular for rotator cuff repair or surgical plication of a capsule. The method utilizes a hand instrument to pass suture through soft tissue, such as a shoulder capsule undergoing plication.

The instrument features a needle slidably disposed in a tubular shaft. The needle is advanced to pierce through the tissue to be repaired. With continued advancement, a hook disposed at the end of the needle engages a length of suture supported ahead of the advancing needle on a prong that extends from the end of the instrument shaft. The needle then is withdrawn, drawing a captured loop of the suture back through the pierced tissue. The suture loop is available for subsequent suturing or knot tying.

More specifically, tissue suturing begins by presenting the instrument, loaded with suture, through an arthroscopic cannula, for example. The operative end of the instrument is positioned, with the needle withdrawn, proximate the tissue to be repaired. The needle then is advanced to pierce the tissue. Further advancement of the needle brings it clear of the pierced tissue to approach a length of suture supported in a slot on the extended prong on the end of the instrument. A hook formed toward the tip of the needle captures the suture. Drawing the needle back pulls a loop of the captured suture through the tissue.

Operation of the instrument is facilitated by additional features of the invention. One handed manipulation of the instrument, for example, is simplified by the provision of a thumb slide. Accordingly, the instrument can be operated using the thumb of one hand to advance the shaft through the tube to pierce tissue, capture the suture, and withdraw the captured suture back through the tissue. The needle may be spring loaded to assist retraction. In addition, the needle shaft can be configured to be withdrawn completely from the instrument to facilitate suture manipulation and withdrawal of the instrument from the patient. Further, the instrument can be made to be disposable, and can be manufactured with a malleable shaft which can be bent into various configurations to facilitate access to tissue.

Other features and advantages of the present invention will become apparent from the following description of the invention which refers to the accompanying drawings.

BRIEF DESCRIPTION OF THE DRAWINGS

FIG. 1 is a perspective view of a tissue suturing instrument according to a preferred embodiment of the present invention.

FIG. 2 is a perspective detail view of the tip of the tissue suturing instrument of FIG. 1.

FIG. 3 is a perspective view of the instrument of FIG. 1, shown with the needle in an advanced position.

FIG. 4 is an enlarged view of the tip of the instrument as shown in FIG. 3.

FIG. 5 is a perspective view of the instrument of FIG. 1 shown loaded with a length of braided suture.

FIG. 6 is an enlarged view of the tip of the instrument as shown in FIG. 5.

FIG. 7 illustrates a step of performing surgical suture plication according to the present invention.

FIG. 8 illustrates a further step of performing surgical suture plication according to the present invention.

DETAILED DESCRIPTION OF THE PREFERRED EMBODIMENT

Figure 9:
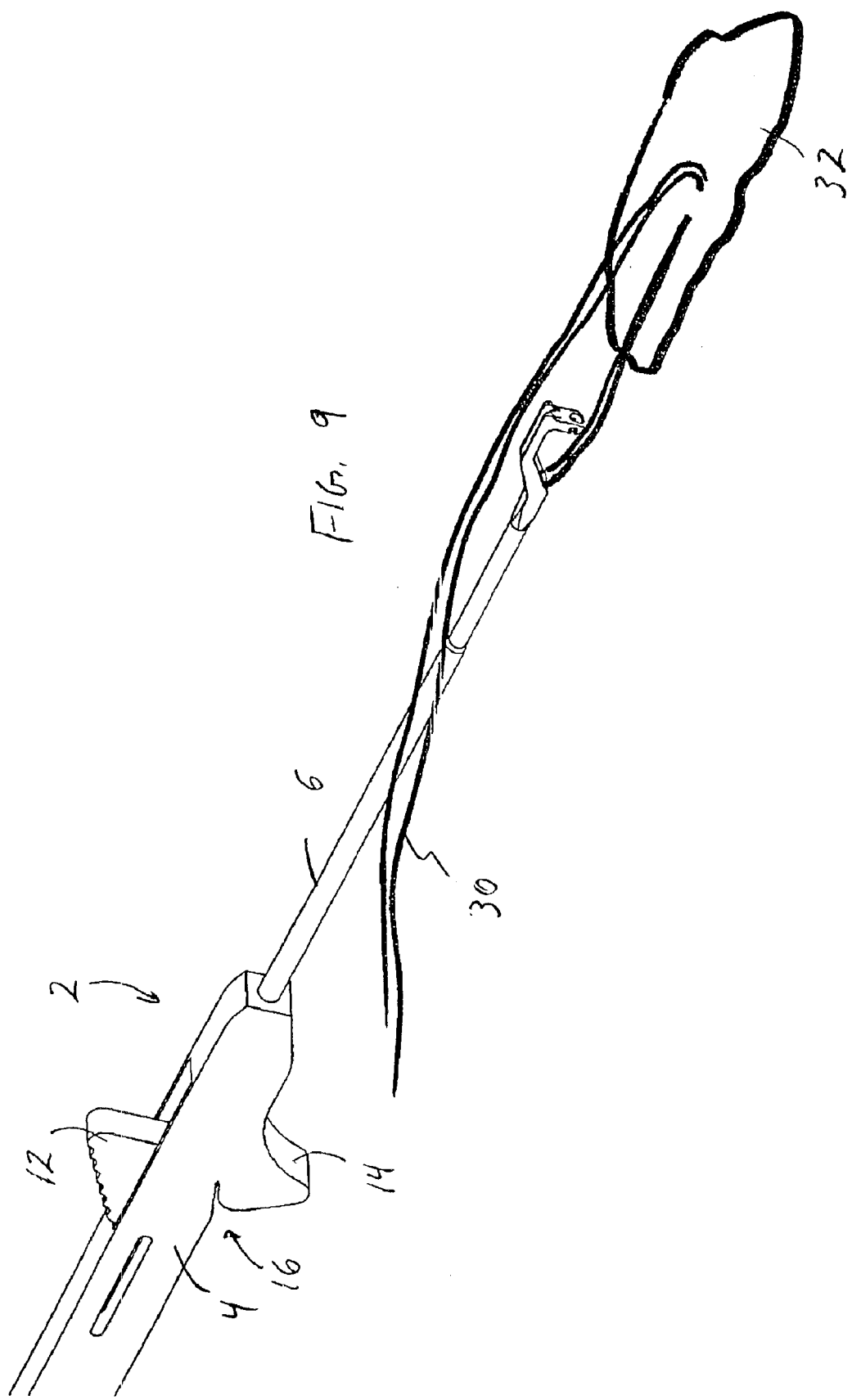
FIG. 9 illustrates an additional step of performing surgical suture plication according to the present invention.

Referring to FIGS. 1–9, a suturing instrument 2 according to a preferred embodiment of the present invention is shown. The instrument includes a handle 4 supporting a cannulated shaft 6. The cannulated shaft 6 terminates in a stationary, prong-shaped tip 8. Optionally, at least a portion of shaft 6 can be bendable, formed of a malleable material, for example, to facilitate directional control of suture placement. A needle 10 extends through shaft 6 and is operated by thumb slide 12. Needle 10 is shown in a retracted position in FIG. 1. Instrument 2 includes a finger support 14 for ease of handling, and a suture pinch slot 16 for capturing tensioned suture, as described below in connection with a preferred surgical procedure using the instrument.

Prong-shaped tip 8 is illustrated in greater detail in FIG. 2. Tip 8 ends in a point 18. Above point 18, tip 8 is configured to define an opening 20 in axial alignment with needle 10. A pair of slots 22 formed in tip 8 on either side of opening 20 are used to capture a section of a suture loop guided through channel 24 formed on the top of tip 8, as described further below.

Referring to FIGS. 3 and 4, instrument 2 is shown with needle 10 in a partially advanced position to reveal hook 26 formed at the end of needle 10. Hook 26 is shaped to capture suture held in slots 22 across opening 20 when needle 10 is advanced into opening 20, as described further below in connection with a preferred method of surgical suturing according to the present invention.

Referring to FIGS. 5 and 6, instrument 2 is shown loaded with a length of braided suture 30 in preparation for performing surgical suturing. Suture 30 is looped through slots 22 across opening 20. The slots 22 face proximally toward needle 10. Two legs of the suture loop are passed separately around the outside of the prong, upwardly and distally, and then together proximally through channel 24 on top of prong 8. Suture 30 is passed along one side of instrument 2 and secured under tension in suture pinch slot 16.

Referring to FIG. 7, a step is illustrated in a preferred procedure for performing surgical plication of a capsule 32. The capsulorrhaphy secures folded pleats of tissue in an effort to reduce laxity in the capsular tissue. Instrument 2 is loaded with suture 30 as described above, and is inserted inferiorly along the capsule. Needle 10 of instrument 2 is maintained in a withdrawn position by manipulation of thumb slide 12, optionally by the urging of a spring loaded inside the handle.

Prong 8 of instrument 2 is shown surrounding a tuck or fold 34 of capsular tissue. The fold is formed by engaging the capsular tissue with pointed end 18 of instrument tip 8 and drawing the instrument back in the direction of arrow A in FIG. 7. The retrograde motion folds a significant amount of tissue into the prong.

Referring to FIG. 8, the preferred capsular plication method proceeds with advancement of needle 10 through the tissue of fold 34. Needle 10 is advanced by the surgeon manipulating thumb slide 12 in the direction of arrow B of FIG. 9. As the end of needle 10 advances through tissue fold 34 and into opening 20, needle 10 engages the portion of suture 30 held across opening 20 between slots 22. Further advancement of needle 10 causes the portion of suture 30 to become captured by hook 26 (FIG. 4).

Referring to FIG. 9, instrument 2 is shown having been withdrawn from capsule 32, leaving suture 30 threaded through capsular tissue in preparation for suture knot tying to secure tightening fold 34. Prior to withdrawing the instrument 2, suture 30 is released from pinch slot 16, and needle 10 is withdrawn from the tissue fold by moving thumb slide 12 back. Suture 30 is then released from hook 26, and tied off to tighten the capsule, or one suture end can be inserted through the eyelet of a suture anchor prior to insertion as a combined capsular plication and Bankart repair.

Although the present invention has been described in connection with capsular plication, the instrument also is useful for other surgical procedures, such as labral and rotator cuff repairs.

While preferred embodiments of the invention has been described and illustrated above, it should be understood that these are exemplary of the invention and are not to be considered as limiting. Additions, deletions, substitutions, and other modifications can be made without departing from the spirit or scope of the present invention. Accordingly, the invention is not to be considered as limited by the foregoing description but is only limited by the scope of the appended claims.

What is claimed is:

1. An instrument for surgical suturing, comprising:
   a shaft;
   a needle disposed slidably for longitudinal travel with respect to the shaft;
   a prong on one end of the shaft, the prong projecting across a longitudinal axis of the needle and having an opening formed through the prong that provides a clearance through which a tip portion of the needle passes when it is advanced; and
   slots formed on a side of the prong facing the end of the shaft and supporting a length of suture on an inner surface of the prong facing the end of the shaft such that the suture extends across the opening formed through the prong, and a longitudinal suture channel formed on a top surface of the prong, the suture channel extending above the longitudinal axis of the needle, the suture being held in the slots by passing strands of the suture separately around sides of the prong and together through the suture channel formed on the top surface of the prong.

2. The instrument of claim 1, further comprising a handle, wherein the shaft is fixed nonslidably to the handle.

3. The instrument of claim 1, further comprising suture supported in the slots across the opening formed through the prong.

4. A hand instrument for soft tissue suturing, the hand instrument comprising:
   a tubular shaft having proximal and distal ends;

a needle disposed slidably within the tubular shaft; and a prong formed on the distal end of the tubular shaft for holding a length of suture in a sliding path of the needle such that a hook formed on the needle captures the length of suture and, upon proximal movement of the needle, the suture is released from the prong, the suture being held in slots formed on a proximal side of the prong facing the end of the tubular shaft by passing strands of the suture separately around sides of the prong and together through a suture channel formed on a top surface of the prong, the suture channel extending above a longitudinal axis of the needle.

5. A method for suturing soft tissue tears using a hand instrument having a tubular shaft, a needle slidably disposed in the tubular shaft and having a hook formed on the distal end, and a prong formed on a distal end of the tubular shaft holding a length of suture, the prong having a suture channel formed on a top surface of the prong and extending above a longitudinal axis of the needle, the method comprising the steps of:

advancing the needle;

engaging the length of suture with the hook in the needle; and sliding the needle proximally such that the length of suture engaged by the hook is released from a proximal face of the prong and drawn back away from the prong.

6. The method of claim 5, further comprising the steps of proximating a tissue tear with the hand instrument.

7. The method of claim 6, wherein the step of advancing the needle includes advancing the needle through tissue.

8. The method of claim 7, wherein the step of sliding the needle proximally comprises drawing a loop of the length of suture engaged by the hook through the tissue.

9. The method of claim 6, wherein the tissue tear is a tear of the meniscus.

10. The method of claim 5, further comprising holding the suture in the slots by passing the suture strands separately back around sides of the prong, then together up through the suture channel formed on the top surface of the prong.

11. The method of claim 10, further comprising the step of securing the strands in a pinch slot formed in a handle of the instrument.

* * * * *